(12) United States Patent
Liu

(10) Patent No.: US 11,219,724 B2
(45) Date of Patent: Jan. 11, 2022

(54) HEATING ELEMENT

(71) Applicant: SHENZHEN BUDDY TECHNOLOGY DEVELOPMENT CO., LTD., Shenzhen (CN)

(72) Inventor: Xiang Liu, Shenzhen (CN)

(73) Assignee: SHENZHEN BUDDY TECHNOLOGY DEVELOPMENT CO., LTD., Shenzhen (CN)

( * ) Notice: Subject to any disclaimer, the term of this patent is extended or adjusted under 35 U.S.C. 154(b) by 340 days.

(21) Appl. No.: 16/381,032

(22) Filed: Apr. 11, 2019

(65) Prior Publication Data

US 2020/0268988 A1      Aug. 27, 2020

(30) Foreign Application Priority Data

Feb. 27, 2019   (CN) .......................... 201910145461.0

(51) Int. Cl.
*A61M 11/04* (2006.01)
*H05B 3/46* (2006.01)
*A24F 40/46* (2020.01)

(52) U.S. Cl.
CPC ............ *A61M 11/044* (2014.02); *H05B 3/46* (2013.01); *A24F 40/46* (2020.01); *H05B 2203/014* (2013.01); *H05B 2203/021* (2013.01)

(58) Field of Classification Search
CPC . A61M 11/044; H05B 3/46; H05B 2203/014; H05B 2203/021; A24F 40/46
See application file for complete search history.

(56) References Cited

U.S. PATENT DOCUMENTS

| | | | |
|---|---|---|---|
| 2015/0136124 A1* | 5/2015 | Aronie | A61M 15/0086 128/202.21 |
| 2016/0021930 A1* | 1/2016 | Minskoff | A24F 40/51 131/329 |
| 2016/0029700 A1* | 2/2016 | Li | A24F 40/44 131/329 |
| 2017/0086506 A1* | 3/2017 | Rado | A24F 40/485 |
| 2017/0224017 A1* | 8/2017 | Li | H05B 1/0244 |

* cited by examiner

*Primary Examiner* — Erin E McGrath
(74) *Attorney, Agent, or Firm* — Bayramoglu Law Offices LLC

(57) ABSTRACT

A heating element including a ceramic body and a heating wire. The ceramic main body includes an upper portion and a lower portion. The upper portion and the lower portion are integrally formed. A plurality of micro-pores for oil penetration are distributed in the upper portion and the lower portion. A shape of a periphery of the upper portion is matched with a shape of an interior of an atomizer for mounting the upper portion. A side of the upper portion is provided with a notch. The shape of the notch is matched with the shape of an air flowing tube of the atomizer. The lower portion extends downward from the side of the upper portion opposite to the notch. The heating wire is mounted to the ceramic main body, and the heating wire extends outward from the bottom of the lower portion.

16 Claims, 4 Drawing Sheets

HEATING ELEMENT

CROSS REFERENCE TO THE RELATED APPLICATIONS

This application is based upon and claims priority to Chinese Patent Application No. 201910145461.0, filed on Feb. 27, 2019, the entire contents of which are incorporated herein by reference.

TECHNICAL FIELD

The present invention relates to the field of atomizers, in particularly relates to a heating element applied to an atomizer.

BACKGROUND

Current atomizers mainly use cotton-coated structure, where the cotton is infiltrated with oil, and the coated cotton is heated for atomization. However, this method has some defects. First of all, the coated cotton causes oil leakage easily, which makes the atomizer get failed or users accidentally inhale the leaked oil. Secondly, during the atomization process, the temperature of the heating wire and the amount of oil atomization are difficult to get balanced, so that the cotton can be scorched easily. Moreover, due to the uneven atomization, it is difficult to achieve an ideal release effect, thereby affecting the taste, in order to improve the taste and avoid accidental inhalation of the oil, some heating elements began to appear on the market. The advantage of the heating elements is to remove the coated cotton. By doing so, the oil can penetrate the micro-pores of the heating element more evenly, and the heating is more uniform. However, now, the heating elements available on the market still have some defects. Most of the heating elements available on the market have a cup-shaped structure, and the inner space of the cup-shaped structure is directly connected to the oil storage chamber. Limited by the cross-sectional area of the atomizer, the area for the heating element to receive the oil is small, so that the oil penetration is uneven, and unsmooth vapor release will be caused frequently. In addition, if the atomizer is configured in the form with separated oil and vapor, usually the vapor channel can only be configured at the edge of the heating element, and the vapor would move along the gap, thereby causing the unsmooth inhalation.

Therefore, it is urgently needed to have a heating element that can solve the problem of accidental inhalation of the oil and meanwhile burn the oil sufficiently to achieve a better atomization effect and improve the feeling during use.

SUMMARY

Regarding the technical problems, the present invention aims to provide a heating element that can solve the problem of accidental inhalations of the oil and meanwhile burn the oil sufficiently to achieve a better atomization effect and improve the feeling during use. The present invention provides a heating element that includes a ceramic main body and a heating wire. The ceramic main body has an upper portion and lower portion, wherein the upper portion and the lower portion are integrally formed. A plurality of micro-pores for oil penetration are distributed in the upper portion and lower portion. A shape of a periphery of the upper portion is matched with a shape of an interior of an atomizer for mounting the upper portion. A side of the upper portion is provided with a notch, and a shape of the notch is matched with a shape of an air flowing tube of the atomizer. The lower portion extends downward from a side of the upper portion opposite to the notch. The heating wire is mounted on the ceramic main body, and the heating wire extends outward from a bottom of the lower portion.

As a preferred solution, an upper surface of the upper portion is provided with an oil inlet groove recessed inward.

As a preferred solution, a side surface of the lower portion on a same side of the notch is provided with an air outlet, and a position of the air outlet is close to the installation position of the lower end of the air flowing tube of the atomizer.

As a preferred solution, two air outlets are configured.

As a preferred solution, the heating element further includes a silicone sleeve covering the outer surface of the lower portion, the silicone sleeve is provided with a through hole at the position of the air outlet, and the end of the heating wire passes through the silicone sleeve.

As a preferred solution, the air outlet is a through hole or a blind hole, and an inner wall of the air outlet is wound with at least one turn of the heating wire.

As a preferred solution, the heating wire is printed or inlaid and fixed to the bottom of the lower portion.

As a preferred solution, the shape of the notch being matched with the shape of the air flowing tube of the atomizer further includes the shape of the notch being matched with a shape of a mounting member of the air flowing tube of the atomizer.

As a preferred solution, a side wall of the periphery of the upper portion is configured with at least one turn of groove recessed inward for placing a sealing ring.

As a preferred solution, an overall shape of the upper portion is configured to be a crescent-shaped column, and a notch of the crescent-shaped column is the notch for the air flowing tube of the atomizer.

The implementation of the present invention can achieve at least the following advantages. The heating element includes an upper portion and a lower portion, so that the upper portion and the lower portion can be formed into different shapes. The shape of the periphery of the upper portion can be configured to match the shape of the interior of the atomizer for mounting the upper portion, thereby maximizing the contact area between the upper surface of the heating element and the oil storage chamber of the atomizer. Thereby, the oil is more evenly distributed in the heating element, the oil is replenished more quickly, and the atomization effect is better. The lower portion extends downward from a side of the upper portion opposite to the notch, so that at the same horizontal position, the lower portion provides space for the passage of the air flowing tube of the atomizer, and the notch of the upper portion provides space for the passage of the air flowing tube as well. By doing so, the vapor can pass through the air flowing tube alone, thereby smoothing the inhalation and improving the feeling during use. A plurality of micro-pores for oil penetration are distributed on the upper portion and the lower portion, so that the heating element can be heated to generate the vapor under full oil absorption, and the atomization effect is better. The upper surface of the upper portion is configured with an oil inlet groove recessed inward to provide a settling passage for the oil in the oil storage chamber, so that the oil can settle to the bottom of the heating element more quickly and contact with the heating wire, thereby shortening the atomization time and achieving a better feeling during use. The side surface of the lower portion on the same side of the notch is provided with an air outlet, and the position of the air outlet is close to the installation position of the lower end of the air flowing tube of the atomizer, so that the generated vapor is close to the lower end of the air flowing tube of the atomizer. When subjected to suction, the vapor can quickly enter the lower end of the air flowing tube of the atomizer and be transmitted to the suction nozzle through the air flowing tube of the atomizer. Two air outlets are provided, which makes the outflow passages for the generated vapor concentrated. Compared with the vapor outlet passage having only one air outlet, the cross-sectional area is larger and atomization effect is better when two air outlets are provided. The outer surface of the lower portion is covered with a silicone sleeve to avoid oil leakage. The heating wire is printed or inlaid and fixed to the bottom of the lower portion. The methods of printing and inlaying have their own advantages. For example, the process of the printing is simple, while the process of inlaying can control the width of the heating wire freely, to facilitate the adjustment of the degree of heating and atomization. Other mounting member for supporting may be provided between the ceramic heating element and the air flowing tube of the atomizer, the shape of the notch being matched with the shape of the air flowing tube of the atomizer may further include the shape of the notch being matched with a shape of a mounting member of the air flowing tube of the atomizer. The side wall of the periphery of the upper portion is configured with at least one turn of groove recessed inward for placing a sealing ring, so that the sealing between the heating element and the oil storage chamber can be ensured.

The present invention will be further described with reference to the drawings and embodiments hereinafter.

DETAILED DESCRIPTION OF THE EMBODIMENTS

Figure 1:
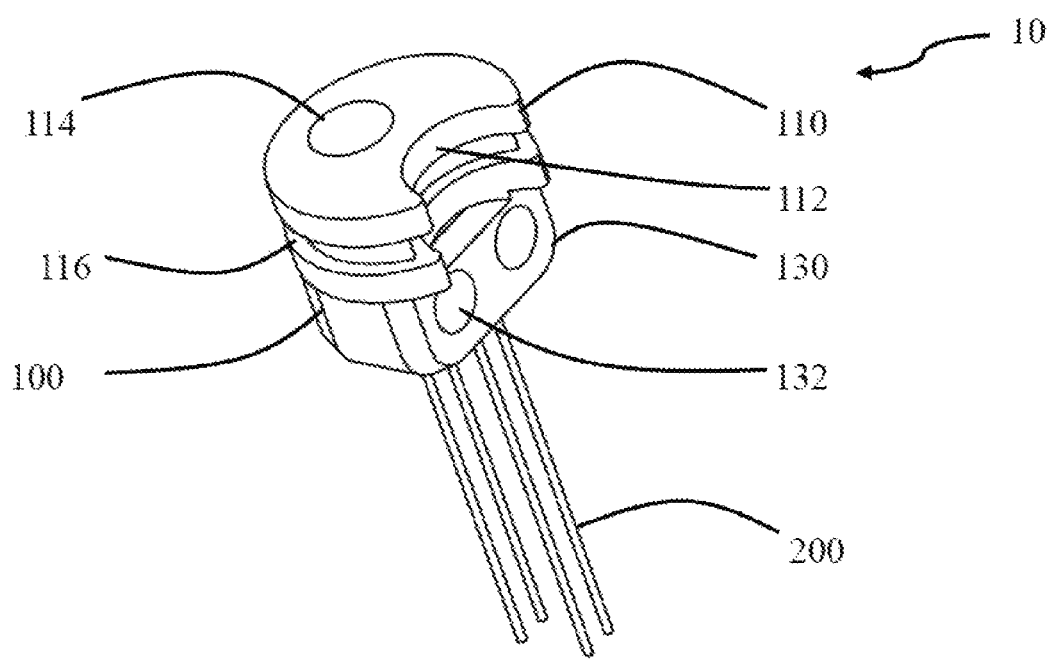
FIG. 1 is a schematic view showing a stereoscopic structure of a heating element provided by the present invention.
Figure 2:
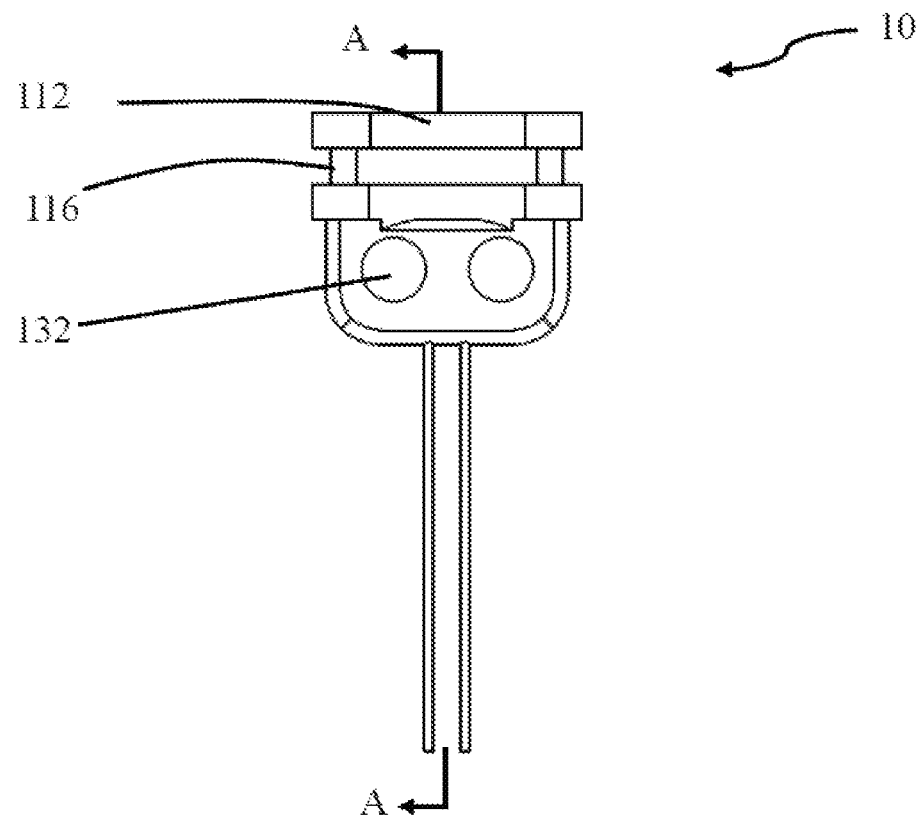
FIG. 2 is a front view of the heating element shown in FIG. 1.
Figure 3:
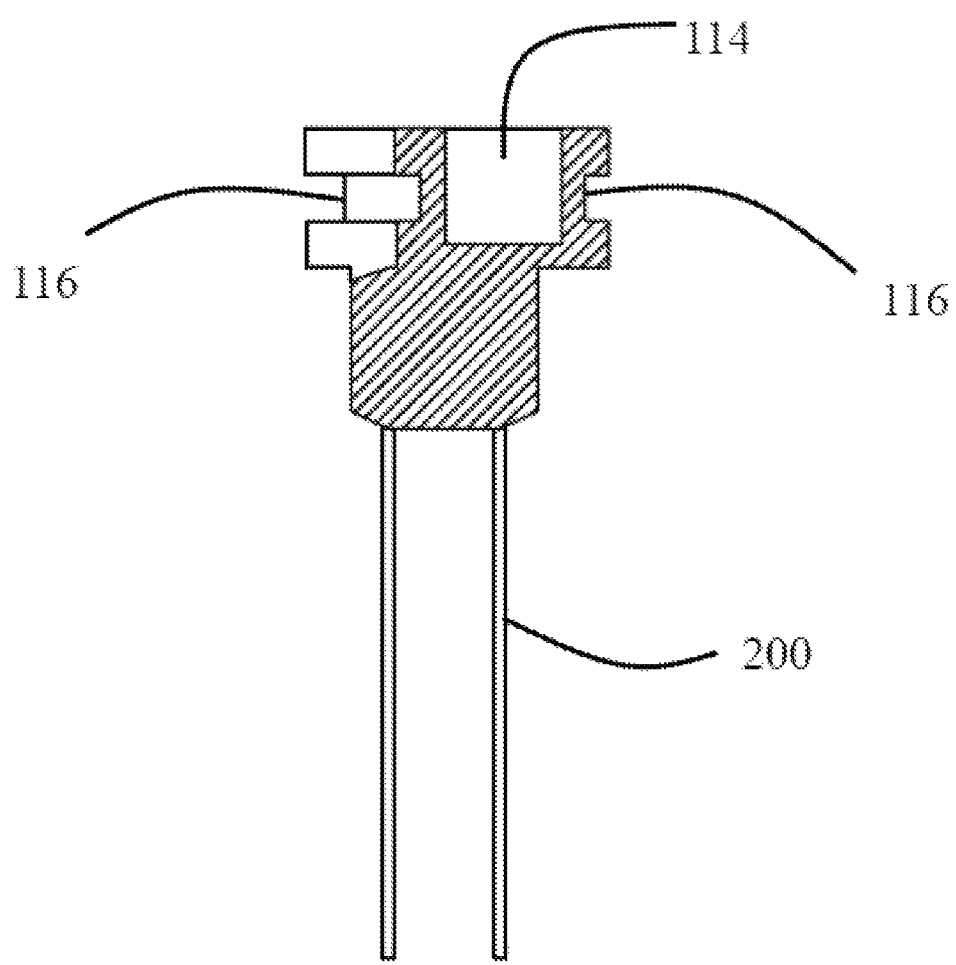
FIG. 3 is a cross-sectional view of the heating element shown in FIG. 2 on the direction of A-A.
Figure 4:
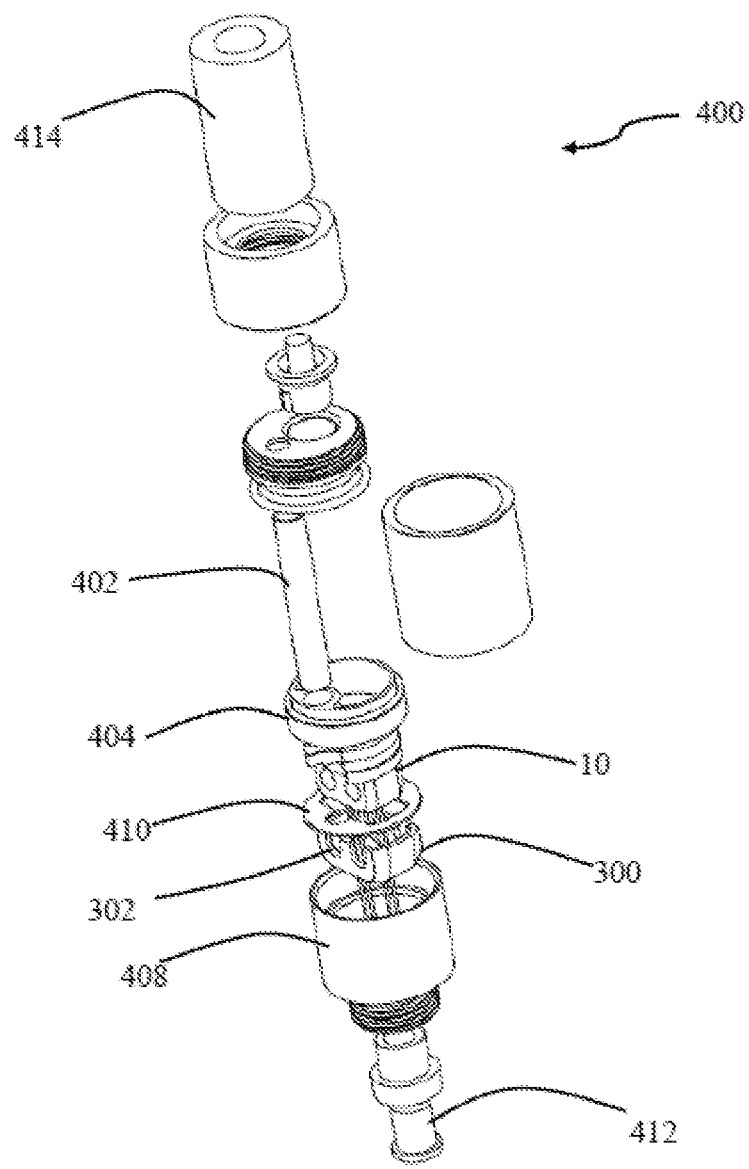
FIG. 4 is an exploded view showing the heating element shown in FIG. 1 applied to an atomizer.
Figure 5:
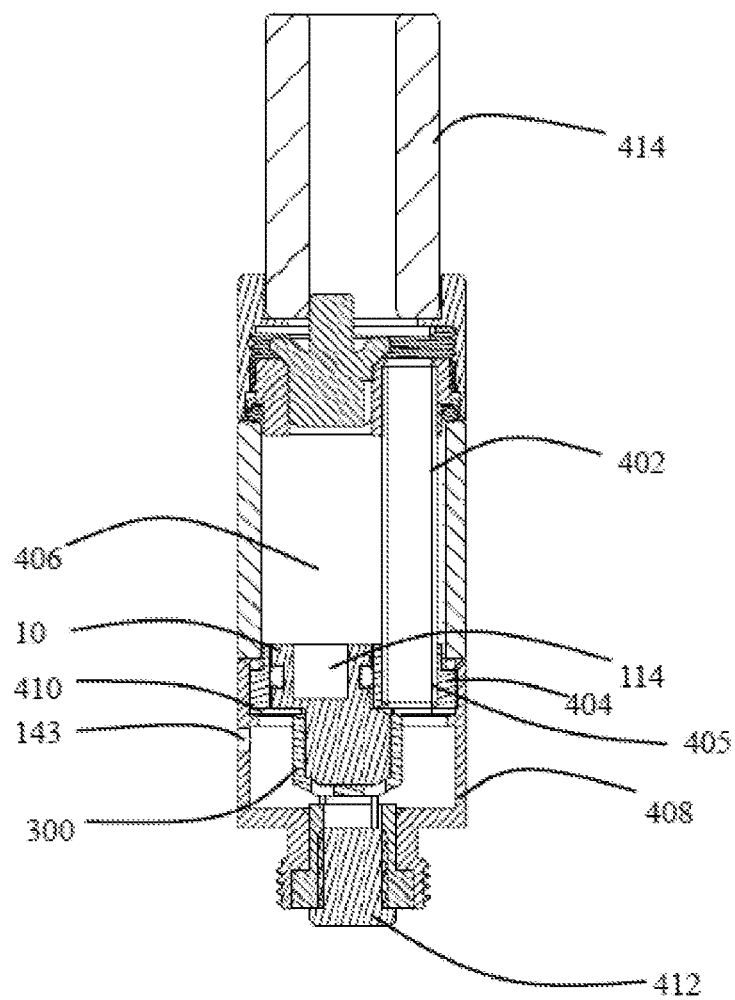
FIG. 5 is a structural schematic view showing the heating element shown in FIG. 4 applied to the atomizer from a longitudinal intermediate section.

Referring to FIGS. 1-5, the first embodiment of the present invention provides a heating element 10 including a ceramic main body 100 and a heating wire 200. The ceramic main body 100 includes an upper portion 110 and a lower portion 130, wherein the upper portion and the lower portion are integrally formed. A plurality of micro-pores for oil penetration (not shown in the drawings) are distributed on the upper portion 110 and the lower portion 130. Preferably, the micro-pores are evenly distributed. A shape of a periphery of the upper portion 110 is matched with a shape of an interior of an atomizer 400 for mounting the upper portion. A side of the upper portion 110 is provided with a notch 112, and a shape of the notch 112 is matched with a shape of an air flowing tube 402 of the atomizer. Further, the shape of the notch 112 may be matched with a shape of a mounting member 404 of the air flowing tube 402 of the atomizer. The lower portion 130 extends downward from a side of the upper portion 110 opposite to the notch 112. The heating wire 200 is mounted on the ceramic main body 100, and the heating wire 200 extends outward from a bottom of the lower portion 130. The heating wire 200 is printed or inlaid and fixed to the bottom of the lower portion 130.

The upper surface of the upper portion 110 is provided with an oil inlet groove 114 recessed inward. The side surface of the lower portion 130 on a same side of the notch is provided with an air outlet 132, and a position of the air outlet 132 is close to an installation position of a lower end of the air flowing tube 402 of the atomizer. In the present embodiment, the air outlet 132 is a through hole running through the heating element 10. Two uniformed turns of heating wires 200 are wound in the air outlet 132 and are connected to the heating wire 200 extending out from the lower portion 130. Winding the heating wire 200 in the air outlet 132 can improve the atomization efficiency, thereby improving the use experience. In the present embodiment, two air outlets are configured. The heating element 10 further includes a silicone sleeve 300 covering an outer surface of the lower portion 130. The silicone sleeve 300 is provided with a through hole 302 at a position corresponding to the air outlet 132.

The side wall of the periphery of the upper portion 110 is configured with at least one turn of groove 116 recessed inward for placing a sealing ring (not shown in the drawings). In the present embodiment, an overall shape of the upper portion is a crescent-shaped column, and a notch of the crescent-shaped column is the notch 112 for the air flowing tube 402 of the atomizer.

The heating element 10 provided by the present invention is mounted to the atomizer 400. Specifically, the heating element 10 is mounted below an oil storage chamber 406, directly connected to the oil storage chamber 406, and embedded in the mounting member 404. The mounting member 404 is further provided with a through hole 405 that allows the air flowing tube 402 of the atomizer to pass through. A base 408 is connected to the lower end of the oil storage chamber 406. A cavity is provided in the base 408 to accommodate the mounting member 404, the heating element 10, the silicone sleeve 300, and a separating piece 410. A pogo pin 412 is mounted on the lower end of the base 408, and the end of the heating wire 200 of the heating element 10 passes through the silicone sleeve 300 and is connected to the pogo pin 412 for energization and heating.

In practical use, the oil is injected into the oil storage chamber 406, and uniformly permeates into the micro-pores of the heating element 10. The heating wire 200 of the heating element 10 is electrified to make the oil in the heating element 10 generate vapor. After the vapor is generated, the vapor emerges from the air outlet 132 in the heating element 10 and passes through the through hole 302 of the silicone sleeve 300 to enter the base 408. The outside air enters from the air inlet 143 of the base 408. When the suction nozzle portion 414 inhales, the outside air enters the air flowing tube 402 together with the vapor generated by the heating element 10, and passes through the air flowing tube 402 and exports from the suction nozzle portion 414.

In other embodiments, any one or more technical features from the oil inlet groove 114, the air outlet 132, and the groove 116 may be removed to provide a suboptimal solution compared with a relatively optimal solution, such a technical solution should also be considered as falling within the scope of the present patent application.

However, the above descriptions cannot be understood as a limitation to the scope of the present patent application. It should be noted that, various modifications and improvements can be derived by people of ordinary skill in the art without departing from the concept of the present invention. For example, different features in various embodiments may be combined. These modifications and improvements should also be considered as falling within the scope of the present invention.

What is claimed is:

1. A heating element, comprising a ceramic main body and a heating wire, wherein the ceramic main body comprises an upper portion and a lower portion, the upper portion and the lower portion are integrally formed; a plurality of micro-pores for an oil penetration are distributed in the upper portion and the lower portion; a shape of a periphery of the upper portion is capable of matching with a shape of an interior of an atomizer for mounting the upper portion a side of the upper portion is provided with a notch, and a shape of the notch is capable of matching with a shape of an air flowing tube of the atomizer; the lower portion extends downward from a side of the upper portion opposite to the notch; and the heating wire is mounted to the ceramic main body, and the heating wire extends outward from a bottom of the lower portion,
wherein a side surface of the lower portion on a same side of the notch is provided with at least one air outlet and a position of the at least one air outlet is below an installation position of a lower end of the air flowing tube of the atomizer.

2. The heating element of claim 1, wherein an upper surface of the upper portion is provided with an oil inlet groove recessed inward.

3. The heating element of claim 1, wherein the at least one air outlet comprises two air outlets.

4. The heating element of claim 3, wherein the heating element further comprises a silicone sleeve covering an outer surface of the lower portion, the silicone sleeve is provided with a through hole at a position corresponding to the at least one air outlet, and an end of the heating wire passes through the silicone sleeve.

5. The heating element of claim 1, wherein the at least one air outlet is a through hole or a blind hole, and an inner wall of the at least one air outlet is wound with at least one turn of the heating wire.

6. The heating element of claim 1, wherein the heating wire is printed or inlaid and fixed to the bottom of the lower portion.

7. The heating element of claim 1, wherein the shape of the notch being matched with the shape of the air flowing tube of the atomizer further comprises the shape of the notch being matched with a shape of a mounting member of the air flowing tube of the atomizer.

8. The heating element of claim 1, wherein a side wall of the periphery of the upper portion is configured with at least one turn of groove recessed inward for placing a sealing ring.

9. The heating element of claim 8, wherein an overall shape of the upper portion is configured as a crescent-shaped column, and a notch of the crescent-shaped column is the notch for the air flowing tube of the atomizer.

10. The heating element of claim 2, wherein a side wall of the periphery of the upper portion is configured with at least one turn of groove recessed inward for placing a sealing ring.

11. The heating element of claim 1, wherein a side wall of the periphery of the upper portion is configured with at least one turn of groove recessed inward for placing a sealing ring.

12. The heating element of claim 3, wherein a side wall of the periphery of the upper portion is configured with at least one turn of groove recessed inward for placing a sealing ring.

13. The heating element of claim 4, wherein a side wall of the periphery of the upper portion is configured with at least one turn of groove recessed inward for placing a sealing ring.

14. The heating element of claim 5, wherein a side wall of the periphery of the upper portion is configured with at least one turn of groove recessed inward for placing a sealing ring.

15. The heating element of claim 6, wherein a side wall of the periphery of the upper portion is configured with at least one turn of groove recessed inward for placing a sealing ring.

16. The heating element of claim 7, wherein a side wall of the periphery of the upper portion is configured with at least one turn of groove recessed inward for placing a sealing ring.

* * * * *